(12) United States Patent
Palti

(10) Patent No.: US 9,023,091 B2
(45) Date of Patent: May 5, 2015

(54) TREATING CANCER USING ELECTROMAGNETIC FIELDS IN COMBINATION WITH PHOTODYNAMIC THERAPY

(71) Applicant: Novocure Ltd, St. Helier (JE)

(72) Inventor: Yoram Palti, Haifa (IL)

(73) Assignee: Novocure Limited, St. Helier (JE)

( * ) Notice: Subject to any disclaimer, the term of this patent is extended or adjusted under 35 U.S.C. 154(b) by 0 days.

(21) Appl. No.: 13/788,159

(22) Filed: Mar. 7, 2013

(65) Prior Publication Data

US 2013/0184637 A1    Jul. 18, 2013

Related U.S. Application Data

(62) Division of application No. 12/042,830, filed on Mar. 5, 2008, now Pat. No. 8,465,533.

(60) Provisional application No. 60/893,173, filed on Mar. 6, 2007.

(51) Int. Cl.
*A61N 1/30* (2006.01)
*A61N 5/06* (2006.01)
*A61B 18/04* (2006.01)
*A61N 1/40* (2006.01)

(52) U.S. Cl.
CPC . *A61B 18/04* (2013.01); *A61N 1/40* (2013.01); *A61N 5/0601* (2013.01); *A61N 5/062* (2013.01); *A61N 2005/0651* (2013.01)

(58) Field of Classification Search
CPC ........ A61N 1/40; A61N 5/0601; A61N 5/062
USPC ............................ 607/80, 88, 92; 604/20, 501
See application file for complete search history.

(56) References Cited

U.S. PATENT DOCUMENTS 6,622,049 B2 * 9/2003 Penner et al. .................... 607/59

* cited by examiner

*Primary Examiner* — Tammie K Heller
(74) *Attorney, Agent, or Firm* — Proskauer

(57) ABSTRACT

A light generating circuit is implanted in a subject's body and aimed at a target region such as a tumor. A photosensitizer is introduced into the target region, and an AC electric field is induced in the region. The field causes the light generating circuit to generate light, which activates the photosensitizer; and at certain field strengths and frequencies, the field itself has a beneficial effect. The beneficial effects of the field and the activated photosensitizer are thereby obtained simultaneously.

9 Claims, 3 Drawing Sheets

TREATING CANCER USING ELECTROMAGNETIC FIELDS IN COMBINATION WITH PHOTODYNAMIC THERAPY

CROSS REFERENCE TO RELATED APPLICATIONS

This application is a divisional of U.S. application Ser. No. 12/042,830, filed on Mar. 5, 2008, now U.S. Pat. No. 8,465,533, which claims the benefit of U.S. provisional application No. 60/893,173, filed Mar. 6, 2007.

BACKGROUND

Drugs and radiation therapy are conventional approaches to treating cancer. One example is Cisplatin or cis-diamminedichloroplatinum(II) (CDDP), which is a platinum-based chemotherapy drug used to treat various types of cancers, including sarcomas, some carcinomas (e.g. small cell lung cancer and ovarian cancer), lymphomas and germ cell tumors. It was the first member of its class, which now also includes carboplatin and oxaliplatin. Cisplatin acts by crosslinking DNA in various different ways, in a manner that is not cell cycle specific, making it impossible for rapidly dividing cells to duplicate their DNA for mitosis. The damaged DNA sets off DNA repair mechanisms, which activate apoptosis when repair proves impossible.

Another example is Paclitaxel, more commonly referred to by the trade name Taxol®, which is a member of the larger family of compounds known as taxanes. Currently, paclitaxel is used in the treatment of breast, ovarian, certain non-small-cell lung cancers, and Kaposi's sarcoma. This potent antineoplastic drug; binds to the N-terminal region of β-tubulin and promotes the formation of highly stable microtubules that resist depolymerization, thus preventing normal cell division and arresting the cell cycle at the $G_2/M$ phase. The microtubule damage induces apoptosis through a JNK-dependent pathway in the early phase followed by a JNK-independent pathway, perhaps related to the activation of protein kinase A or of Raf-1 kinase, that results in phosphorylation of Bcl-2. Major metabolite in human liver microsome is 6α-hydroxy-paclitaxel (6α-OHP). This enzymatic conversion can be used as a potential marker reaction for human CYP2C8.

An additional cancer treatment modality that has been introduced recently is Photo-Dynamic Therapy (PDT). PDT is a rapidly growing area of medical treatment. The diseases that can be successfully treated by PDT include skin cancer, brain tumors, tumors under the surface of the skin, and tumors located on the lining of internal organs. Photodynamic Therapy involves the use of light-activated dyes (photosensitizers) that preferably localize in target cells (e.g. in tumors) but not in normal, healthy cells. Photosensitizers utilize energy from treatment light to produce a cytotoxic oxygen species which kills cancerous or diseased cells. This toxic oxygen species is not a radical but is actually an excited state of oxygen. The excited state is more reactive than ordinary oxygen, and the atoms are in a different quantum spin state than is normally the case. PDT may also work by destroying the blood vessels that feed the cancer cells and by helping the immune system to attack the cancer.

PDT, using the drug Photofrin®, has now been approved as a therapy for a limited number of applications in various parts of the world including the UK and it is now clear that there are some indications where PDT is at least as good as and possibly better than alternative treatments. However it has to be emphasized that PDT is still largely an experimental therapy and is currently only applicable to a very small range of patients. This limitation results in part from the fact that most tumors are located in areas where light from external sources is not effective. To overcome this problem catheters, having light sources at their tip, are inserted through the skin (or a natural cavity like the GI tract) into the body.

Depending on the part of the body being treated, the photosensitizing substances are either injected intravenously into the diseased area or applied to the skin. The photosensitizer selectively accumulates in the tumor region. After allowing time for the accumulation to occur, a light source is applied to the area to be treated. The light causes the drug to react with oxygen, which forms a chemical that kills the cancer cells. Because blood and melanin are relatively absorptive in the shorter visible wavelengths, it is preferable to use infrared light. Therefore, the ideal photosensitizer has an absorbance peak in the infrared part of the spectrum. This ensures that light used in the treatment is able to penetrate maximally through healthy tissue to arrive at the tumor. However, other wavelengths can be selected according to the absorption and sensitivity of the various substances used.

Light-emitting diodes (LEDs) are considered an appropriate light source for PDT. LEDs have a relatively narrow bandwidth (usually 20 to 30 nm), and are available in a wide range of wavelengths, including the near infrared (NIR) and infrared (IR)—from 650 nm to 950 nm. The flexibility provided by chip-on-board techniques makes it possible to fabricate customized LED illuminators for various PDT applications.

In more established Photodynamic Therapy treatments, such as skin cancer therapy, the diseased zone is exposed to an LED area light for a precisely calculated exposure time. In newer or more experimental areas of treatment, miniature LED arrays are actually implanted into tissue, or are placed on catheters and are moved through the body. In some procedures, LED dice are fixed to a flexible, compact substrate. However, for any tumor situated more than about 1 cm away from the accessible surface, the light source must be implanted. Since LEDs must be hooked up to a power supply in order to function, this generally requires that lead wires connect the LED or other light source to an external device. As the duration of an effective treatment may be long, even weeks, the wires that penetrate the skin may lead to contamination, dysfunction and significant discomfort.

SUMMARY OF THE INVENTION

A light generating circuit is implanted in a subject's body and aimed at a target region such as a tumor. A photosensitizer is introduced into the target region, and an AC electric field is induced in the region. The field causes the light generating circuit to generate light, which activates the photosensitizer and the field itself also has a beneficial effect. The beneficial effects of the field and the activated photosensitizer are thereby obtained simultaneously.

DETAILED DESCRIPTION OF THE PREFERRED EMBODIMENTS

As described in U.S. Pat. Nos. 6,868,289 and 7,016,725 each of which is incorporated herein by reference, and in U.S. patent application No. 11/111,439 (filed Apr. 21, 2005) and Ser. No. 11/537,026 (filed Sep. 29, 2006), each of which is incorporated herein by reference, intermediate frequency (100-300 kHz) alternating electric fields, termed TTFields, damage as well as inhibit the growth of numerous types of cancer cells in vitro and in vivo. The efficacy of the treatment is enhanced by sequentially applying fields of varying directions and by the use of special insulated electrodes.

TTFields act by two mechanisms of action: First, they disrupt the normal polymerization-depolymerization process of the spindle microtubules during mitosis. Secondly, they cause a physical disruption of cells towards the end of cytokinesis by producing a unidirectional force on all charge, polar and polarizable intracellular constituents, pushing them towards the narrow neck between the two daughter cells. See Kirson, E. D., et al., *Disruption of cancer cell replication by alternating electric fields*, Cancer Res., 2004. 64(9): p. 3288-95, which is incorporated herein by reference.

The therapeutic efficacy of TTFields was found to be high and the therapeutic index extremely high (no side effects), however, treatment duration was relatively long and the required field intensities were relatively high. In order to improve the treatment efficacy, this invention is designed to enhance the treatment efficacy of TTFields by combining them with photodynamic treatment, PDT.

PDT, or Photodynamic Therapy involves the use of light-activated dyes (photosensitizers) that preferably localize in target cells (e.g. in tumors) but not in normal, healthy cells. When illuminated by a source of appropriate light, the photosensitizers utilize energy from the illumination light to produce cytotoxic agents such as oxygen species which kill cancerous or diseased cells.

In some preferred embodiments, LEDs are used to provide the illumination, and the LEDs are activated by the TTFields (instead of using lead wires connected to a power supply). A single LED or multiple LEDs wired in parallel may be used to provide the illumination.

Figure 1:
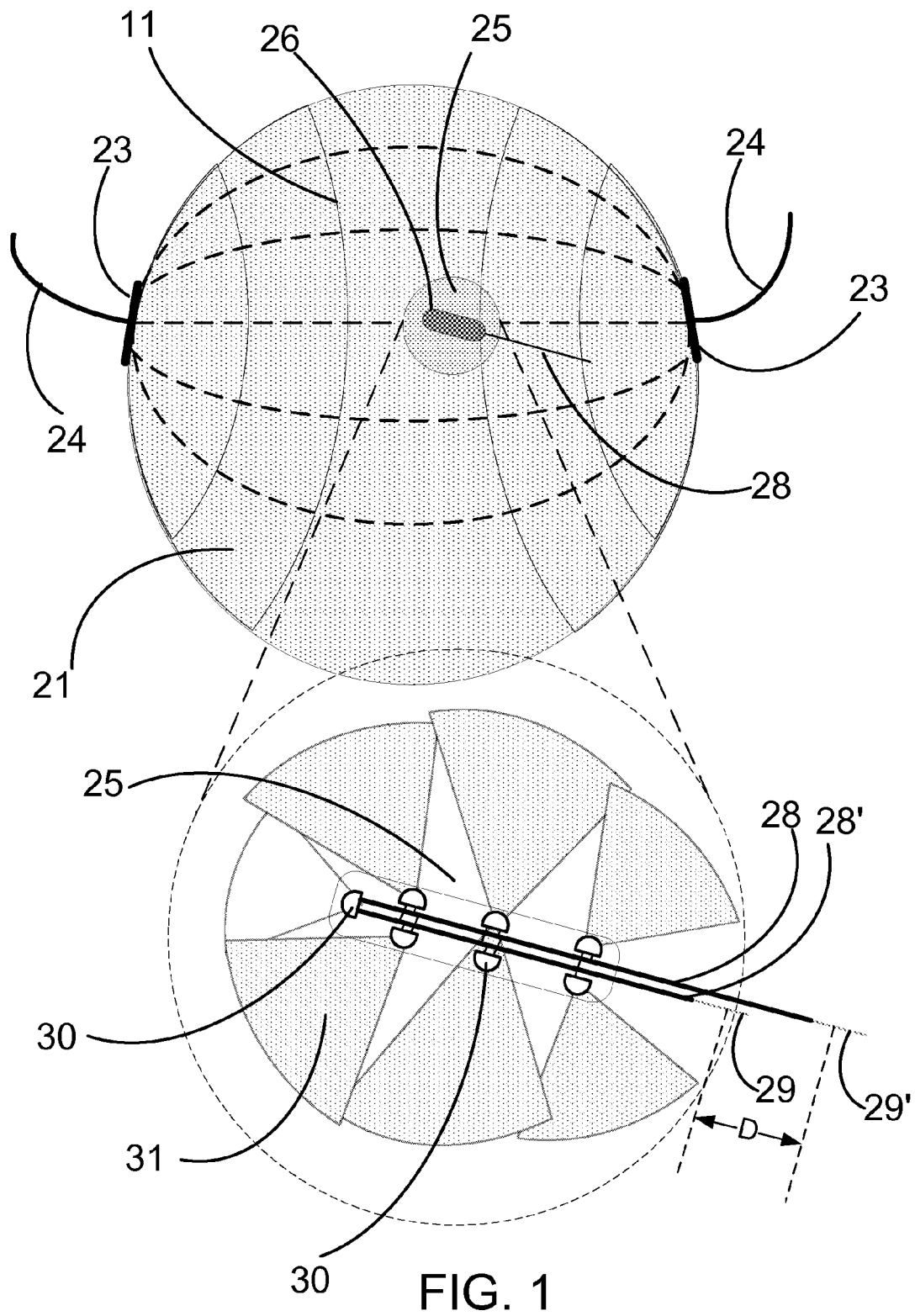
FIG. 1 is a schematic illustration of an implantable illumination assembly with multiple LEDs.

FIG. 1 depicts a schematic layout of a system that uses multiple LEDs 30 wired in parallel that are built into an assembly 26 that is implanted in the treated body 21 near a internal tumor 25. As described in U.S. Pat. Nos. 6,868,289 & 7,089,054, TTF treatment is preferably achieved using special insulated electrodes 23 placed on the body 21 surface. According to one exemplary embodiment, the apparatus for applying the electric field is an electronic apparatus that generates the desired electric signals in the shape of waveforms or trains of pulses. The electronic apparatus includes a generator that generates an alternating voltage waveform at frequencies in the range from about 50 KHz to about 500 KHz. The generator is operatively connected to conductive leads 24 which are connected at their other ends to insulated conductors/electrodes 23 (also referred to as isolects) that are activated by the generated waveforms. The insulated electrodes 23 consist of a conductor in contact with a dielectric (insulating layer) that is in contact with the conductive tissue, thus forming a capacitor. Because the electrodes 23 act like capacitors, the AC electric fields are capacitively coupled into the target region. The insulation on the electrodes 23 preferably has an extremely high dielectric constant such that in the frequency range used, preferably 100 KHz to 500 KHz, the impedance of the insulation on the face of the electrodes 23 is significantly smaller than that of the tissues such that most of the potential drop is on the tissues. The preferred field intensities for TTF treatment are in the range of 1-10V/cm. Thus, if the leads 28, 28' and the corresponding exposed contact points 29, 29' of the LED assembly 26 are positioned at a proper orientation relative to the electric field direction, and the distance D between them is such that the potential difference is about 2-5V (as indicated by the equipotential lines 11), the LEDs 30 will light up when the AC field is applied.

Because the LEDs 30 light up when the AC field is applied, the illumination is provided simultaneously with treatment by the TTFields. Thus, when a proper sensitizing agent is present in the tumor, one obtains the combined TTF plus PDT therapeutic effects simultaneously. The inset of FIG. 1 depicts the details of the LED assembly implanted in the tumor 25. In this case the light beams have conical shape 31, and are oriented to cover most of the tumor area. The number and positions of the individual LEDs 30 can be adjusted for the application at hand to cover the whole tumor area.

Figure 2:
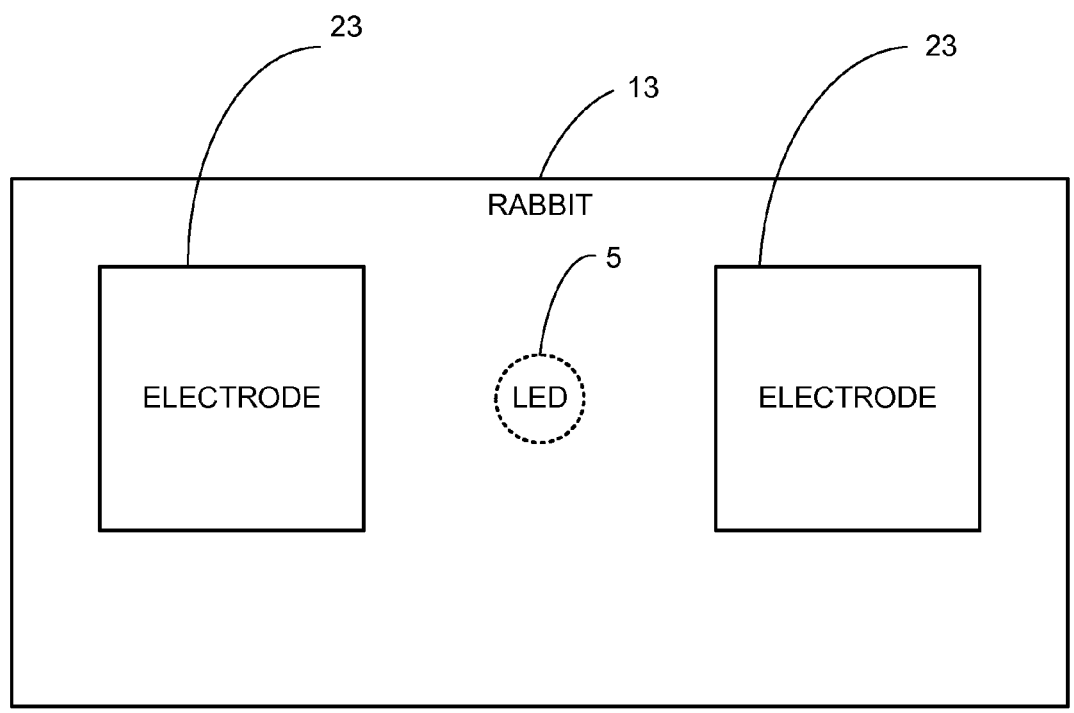
FIG. 2 is a schematic representation of an experiment in which an LED was implanted in a rabbit, and turned on by the application of an AC field.

FIG. 2 is a schematic representation of experiments in which a single LED 5 was implanted in a rabbit 13 and TTFields were applied to the rabbit by means of external insulated electrodes 23. When the field was not applied, the LED 5 remained off. When the field was applied, the implanted LED 5 lit up, and a spot of illumination was visible through the rabbit's intact skin.

Typical LEDs generate significant light output at current of about 2-10 mA, with a voltage drop across the LED in the range of about 2-5 V. That means that its forward resistance is about 1 K$\Omega$ (The reverse resistance is obviously much higher.) If the contact area between each of the metal contacts, which are connected to the two LED leads, is about 1 mm$^2$ or more, the contact resistance will only be a few Ohms. Typical tissue (e.g., muscle) has a specific resistance of 100 $\Omega$-cm. Thus, if one uses fields of 1 V/cm or more, when the trajectory of the distance D between the contact points along the lines if the field is in the order of 2 cm or more, the potential drop between the contact points will be 2 V or more, which is sufficient to light up the LED.

Figure 3:
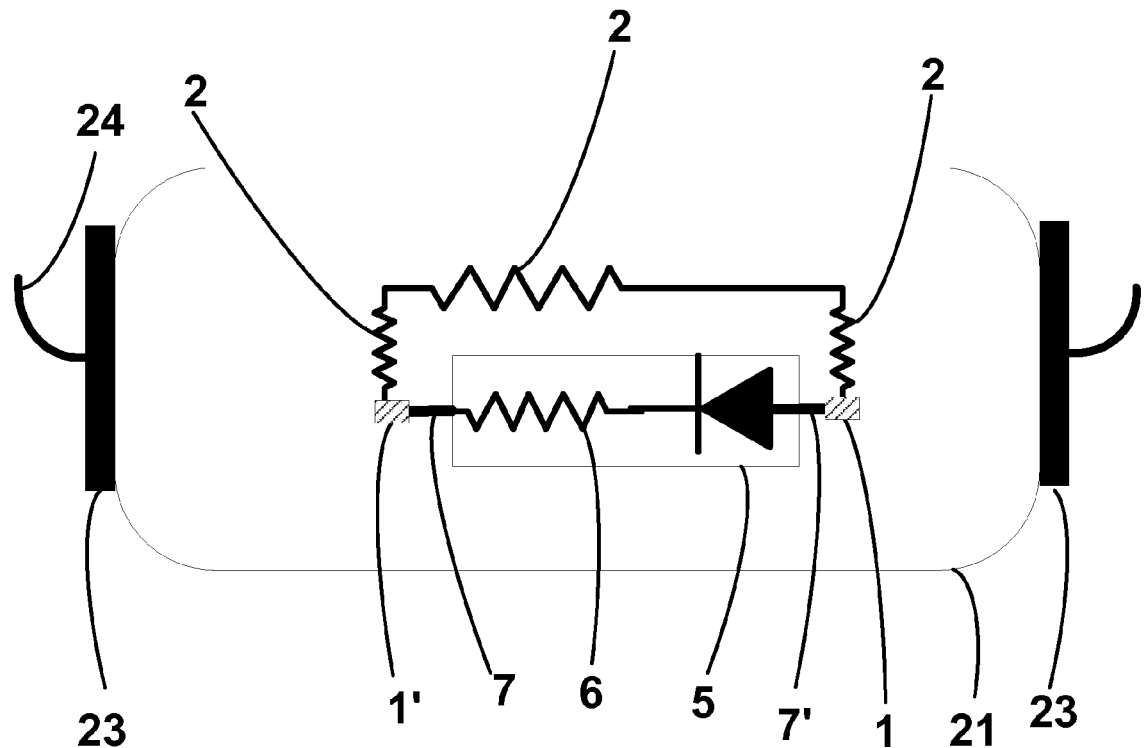
FIG. 3 depicts an equivalent circuit for an implanted LED.
Figure 4:
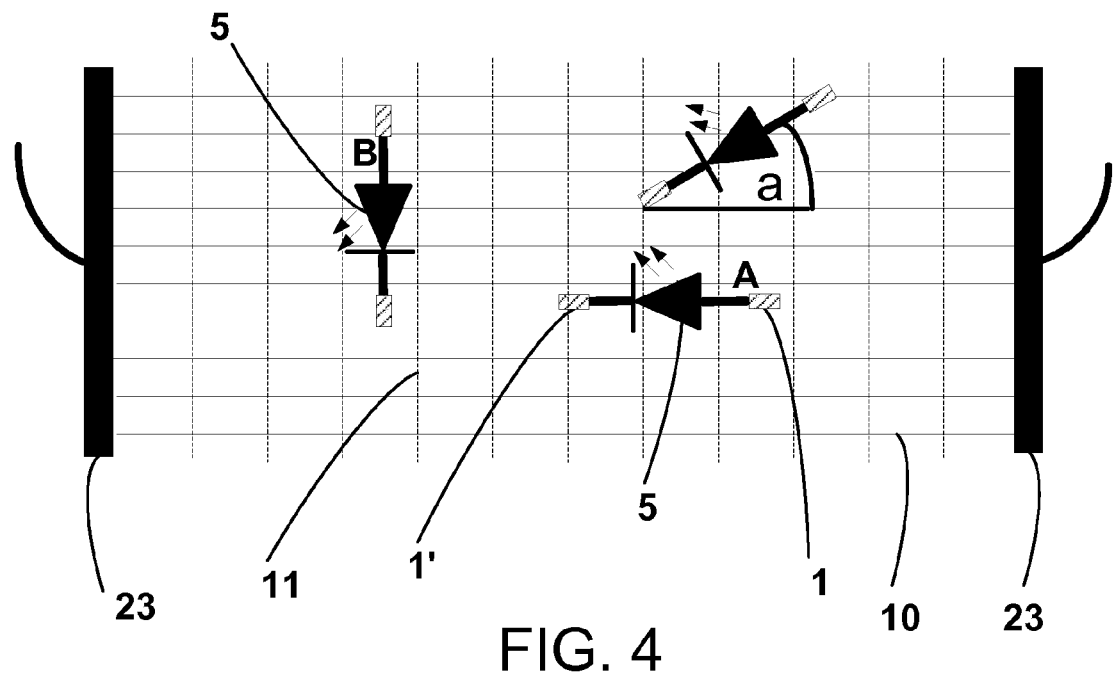
FIG. 4 depicts the impact of the orientation of the LED with respect to the field.

In FIGS. 1, 3, and 4, similar numbering is used to represent corresponding items. FIG. 3 depicts an equivalent circuit for a single LED 5 with leads 7 terminating in contact points 1. Note that resistances 2, 6 indicated in this figure are not actual resistors—rather, they are the resistances of an equivalent circuit, where resistance 6 represents the forward resistance of the LED, and resistance 2 represents the resistance of the tissue in which the LED is implanted, which is in parallel with the LED. Since the LED's forward resistance 6 is significantly larger that the resistance 2 of the tissue (on the order of 1000$\Omega$ for the LED vs. 100$\Omega$ for the tissue) and is also significantly larger that the resistance of the contacts, the forward resistance 6 of the LED does not affect the potential drop to a significant level, so the LED current will be the required 2 mA when the LED sits in a 1 V/cm field with its contacts spaced apart by a distance of 2 cm. Distances for the contact spacing between 0.5 and 5 cm are preferred. For fat tissue or brain, where the specific resistance may be 500 $\Omega$-cm, the field intensity or distance between contacts should be increased to compensate.

FIG. 4 illustrates the impact of the orientation of the LED with respect to the field. The LED 5 must be oriented so that the potential difference between the two contact points 1, 1' is adequate to get the LED 5 to turn on. In a homogeneous field the parallel orientation (orientation A in FIG. 5) is optimal, and this is the orientation that was used in the rabbit experiment depicted in FIG. 2. If the LED is oriented at a different angle with respect to the field, the resulting potential difference is a function of the cosine of the angle between the line connecting the contact points and the field direction (angle a in FIG. 4). Note that the distance between the contacts may be set to a particular value in anticipation of the field intensities that will be generated in the tissue.

When the LED axis is oriented parallel to the field generating electrodes (orientation B in FIG. 4), the orientation of the contact points is normal to the lines of force 10, i.e. parallel to the equipotential lines 11, and no voltage is induced across the LED, so it will not illuminate. This characteristic, taken together with the LED turn-on threshold voltage can be used to turn the illumination on or off as required. For example, when only TTFields treatment is required with no PDT, the field orientation or intensity can be adjusted such that the potential difference between the LED contacts will remain below the LED turn-on threshold.

Optionally, a resistor or an active circuit can be added to adjust the potential drop to an optimal level. Optionally, a suitable current limiting and voltage limiting circuit may be used to prevent the LED from burning out, the design of which will be apparent to persons skilled in the relevant arts. For example, a resistor may be added in series with the LED, with a Zener diode wired in parallel with the series combination of the resistor and the LED. Two Zener diodes of opposite polarity may be used to take care of both forward and reverse voltages.

Practically any standard LED can be used, but the spectral emission of the LED should preferably be matched to the optimal absorption or activation spectrum of the molecule sensitized by the light. In cases where the absorption spectra can not be matched by an LED, white light emitting LEDs can be used. Examples of suitable LEDs include the HLMP-CW24-SV0 from Agilant Technologies, the NSPW300BS from Nichia, and the TLHB440, TLHG440, TLHO440, TLHP440, TLHR440, TLHY440 Series of LEDs from Vishay.

An advantage of this combination is the dual therapeutic effect and the fact that both effects can be obtained in internal organs without the need to use wire leads that penetrate the body surface (skin or other types of lining).

In alternative embodiments the LEDs may be replaced by other light sources. These may include: low voltage incandescent lamps, fluorescent light source, halogen light source, etc. Also voltage sensitive dyes, as part of the implant, or as chromophores added to the photosensitizers or as part of molecules injected to the patient together with the photosensitizers so as to bind to similar cells. The voltage sensitive dyes, bound to molecules or other entities that bind to the relevant cells for long periods of time, can also be used systemically or locally.

Since TTFields show no systemic toxicities, the fields can be used in conjunction with other anti-cancer treatments with a synergistic effect due to the different mechanisms of action by which the various treatments act. Examples of other anti-cancer treatments that can be combined with TTFields include, but are not limited to, five general categories:

The first categories is surgery, including but not limited to open surgery, laparoscopic surgery, minimal resection surgery, debulking surgery, complete resection surgery, etc.

The second category is local ablation techniques including but not limited to radio-surgery, RF ablation, and focused ultrasound.

The third category is ionizing radiation using various dosing and focusing regimen including but not limited to whole organ radiation (e.g. brain), regional radiation (e.g. Y shaped), focal radiation, single dose radiation, fractionated dose radiation, and hyper-fractionated dose radiation.

The fourth category is chemotherapy, including but not limited to {a} Alkylating agents that act mainly by forming covalent bonds between DNA bases, including but not limited to Nitrogen Mustards (e.g., Cyclophosphamide), Aziridines and Epoxides (e.g., Thiopeta), Alkyl Sulfonates (e.g., Busulfan), Nitrosureas (e.g., BCNU and CCNU), Hydrazine and Triazine derivatives (e.g., Procarbazine and Temozolomide); {b} Cisplatin and its analogs that act by forming DNA adducts which lead to intra-strand and inter-strand linking leading to the formation of DNA filaments, including but not limited to Carboplatin, Cisplatin, and Oxaliplatin; {c} Antimetabolites including but not limited to Folate metabolism inhibitors (e.g., Methotrexate, Trimetrexate, Tomudex), 5-fluoropyrimidines (e.g., 5-FU), Oral Fluoropyramidines (e.g., Tegafur, Uracil, Capecitabine), Necleoside analogs (e.g., Cytarabine), Gemcitabine, and 6-thiopurines (e.g., 6-MP and 6-TG); {d} Topoisomerase Interactive Agents that affect the topologic states of DNA by interfering or modulating DNA cleavage, strand passage and re-ligation, including but not limited to Epipodophyllotoxins (e.g., Etoposide and Teniposide), Camptothecin Analogs, Anthracyclines (e.g., Doxorubicin, Daunorubicin, Epirubicin, Idarubicin), Mitoxantrone and Losoxantrone, and Dactinomycin; {e} Antimicrotubule Agents, which interfere with the proper polymerization/depolymerization of microtubules, including but not limited to Vinca alkaloids (e.g., Vincristine, Vinorelbine and Vinblastine), Taxanes (e.g., Paclitaxel, Docetaxel), and Estramustine Phosphate; and {f} Numerous miscellaneous agents exist which cannot be classified into any of the above groups, including but not limited to Suramin, Bleomycin, L-Asparaginase, and Amifostine.

The fifth category is biological therapies, including but not limited to {a} Inteferons; {b} Interleukin-2; {c} Hormonal therapies including but not limited to Tamoxifen, Toremifene, Raloxifene, Medroxyprogesterone and Megestrol, Aromatase inhibitors, GNRH analogues, Antiandrogens, Diethylstilbesterol and Estradiol, and Octreotide; {d} Differentiation agents that catalyze the differentiation of cancerous cells into their mature (differentiated) forms and then to programmed cell death, including but not limited to Retinoids (e.g., All-Trans-Retinoic Acid), Arsenic Trioxide, Histone Deacetylase inhibitors, Vitamin D, and Cytokines; {e} Therapeutic Monoclonal Antibodies; and {f} Antiangiogenesis agents (e.g., VEGF inhibitors).

Since TTFields show no systemic toxicities, it appears that TTFields can be applied to patients before, during and/or after any other anti-cancer treatment to attack the cancer using two different modalities. In addition, it may be possible to lower the toxicity of current anti-cancer treatments by using lower doses of these agents together with TTFields, and still maintain the existing efficacy profile. The dosages, strengths, and timing of the various treatments may be changed to optimize the results that are desired. Note that the most beneficial combination regimen may differ considerably depending on the type of cancer treated, the exact stage of the disease and the type of anticancer treatment used, it should be relatively simple to determine the best combination regimen experimentally. TTFields can also be applied together with more than one of the other anti-cancer approaches (e.g., with PDT plus another therapy).

Note that above-described embodiments are merely preferred implementations of the invention, and numerous alternative embodiments and variations will be apparent to persons skilled in the relevant arts, and are included within the scope of the invention.

I claim:

1. An apparatus for simultaneously exposing a target region within a subject's body to light and an electric field, the subject's body having an internal resistance, the apparatus comprising:

at least two electrodes configured so that when the at least two electrodes are applied to a surface of the subject's body and driven by an AC voltage source, an AC electric field is capacitively coupled into the target region within the subject's body;

an AC waveform generator operatively connected to the at least two electrodes, the AC waveform generator having a frequency between about 50 kHz and about 500 kHz; and a light-emitting assembly that is adapted for implantation within the subject's body, the light-emitting assembly having a first terminal and a second terminal, wherein the light-emitting assembly has a forward resistance that is significantly larger than the internal resistance of the subject's body, and wherein the light-emitting assembly is configured to emit light when the first terminal and the second terminal are positioned with respect to the AC electric field so that an AC voltage gradient of 2 V or more appears between the first terminal and the second terminal.

2. The apparatus of claim 1, wherein the light-emitting assembly comprises a light-emitting diode.

3. The apparatus of claim 1, wherein the first terminal and the second terminal are spaced apart by a distance of between 0.5 and 5 cm.

4. The apparatus of claim 1, wherein a surface of the at least two electrodes that contacts the subject's body is insulated.

5. The apparatus of claim 1, wherein the light-emitting assembly comprises a plurality of light-emitting diodes wired in parallel.

6. The apparatus of claim 1, wherein the AC waveform generator has a frequency between 100 and 500 kHz.

7. The apparatus of claim 1, wherein the AC electric field has an intensity between 1 and 10 V/cm in the target region.

8. The apparatus of claim 7, wherein the first terminal and the second terminal are spaced apart by a distance of 2 cm or more.

9. The apparatus of claim 1, wherein the first terminal and the second terminal are spaced apart by a distance of 2 cm or more.

* * * * *